US00PP20529P2

(12) United States Plant Patent
Hoekert

(10) Patent No.: US PP20,529 P2
(45) Date of Patent: Dec. 8, 2009

(54) ***CALLUNA* PLANT NAMED 'NR 5157'**

(50) Latin Name: *Calluna vulgaris*
Varietal Denomination: Nr 5157

(76) Inventor: Hendrick Cozijn Hoekert, Eden's Creations, Zulderzoestraatweg 410, Wezep (NL)

( * ) Notice: Subject to any disclaimer, the term of this patent is extended or adjusted under 35 U.S.C. 154(b) by 0 days.

(21) Appl. No.: 12/284,504

(22) Filed: Sep. 23, 2008

(51) Int. Cl.
*A01H 5/00* (2006.01)

(52) U.S. Cl. ..... Plt./231
(58) Field of Classification Search ..... Plt./231, Plt./226
See application file for complete search history.

*Primary Examiner*—June Hwu
(74) *Attorney, Agent, or Firm*—Penny J. Aguirre

(57) ABSTRACT

A new cultivar of *Calluna vulgaris,* 'Nr 5157', characterized by its upright plant habit, its bud flowering habit imparting a long flowering period, its densely packed pink-purple flower buds, its vigorous growth habit, and its cold hardiness to U.S.D.A. Zone 4.

2 Drawing Sheets

Botanical classification: *Calluna vulgaris.*
Variety denomination: 'Nr 5157'.

BACKGROUND OF THE INVENTION

The present invention relates to a new and distinct cultivar of *Calluna vulgaris* and will be referred to hereafter by its cultivar name, 'Nr 5157'. 'Nr 5157' is a new cultivar of evergreen shrub grown for use as a landscape plant.

The new Invention arose as the result of an ongoing controlled breeding program by the Inventor in Wezep, The Netherlands. The goal of the breeding program is to develop new cultivars of *Calluna* that combine an upright growth habit and flowers that exhibit strong, bright colors with a bud flowering habit. 'Nr 5157' was selected as a single unique plant by the Inventor in September 2005 in a test garden in his nursery his nursery in Wezep, The Netherlands. 'Nr 5157' arose from a cross made in September 2003 between a proprietary female parent designated by accession No. K4001 and a proprietary male parent designated by accession No. 23E3 (both unnamed and unpatented).

Asexual reproduction of the new cultivar was first accomplished by the Inventor using stem cuttings in September of 2005 in Wezep, The Netherlands. The characteristics of 'Nr 5157' have been determined to be stable and are reproduced true to type in successive generations.

SUMMARY OF THE INVENTION

The following traits have been repeatedly observed and represent the characteristics of the new cultivar as grown outdoors in trial beds and containers in Wezep, The Netherlands. These attributes in combination distinguish 'Nr 5157' as a unique cultivar of *Calluna.*

1. 'Nr 5157' exhibits an erect, upright growth habit.
2. 'Nr 5157' exhibits stems that are densely covered with flowers that are pink-purple in color.
3. 'Nr 5157' exhibits a bud flowering habit, which imparts a long flowering period.
4. 'Nr 5157' exhibits a vigorous growth habit.
5. 'Nr 5157' is cold hardy to U.S.D.A. Zone 4.

'Nr 5157' differs from its parent plants in having a more consistently erect growth habit and in having more densely packed flowering buds. The closest comparison cultivars for 'Nr 5157' are cultivars from the same breeding program that are similar in plant and flowering habit, 'NR 580' (U.S. Plant patent application Ser. No. 12/284,505) and 'NR 5163' (U.S. Plant patent application Ser. No. 12/284,556). 'Nr 580' differs in having flowers that are clear white in color while 'Nr 5163' differs in having flowers that are red-purple in color. 'Nr 5157' can also be compared to the cultivar 'Ralph Purnell' (not patented). 'Nr 5157' is unique from 'Ralph Purnell' in that 'Ralph Purnell' has a more spreading, open, less upright plant habit and flowers that are less dense, light pink in color, and that open. The flowers of 'Nr 5157' remained closed (bud flowering) and therefore 'Nr 5157' blooms for a longer period of time.

BRIEF DESCRIPTION OF THE DRAWING

The accompanying colored photographs illustrate the overall appearance and distinct characteristics of a 2 year-old plant the new *Calluna* as grown outdoors in a 10 cm container in Wezep, The Netherlands.

The photograph in FIG. 1 illustrates the overall appearance of 'Nr 5157' in bloom.

Figure 2:
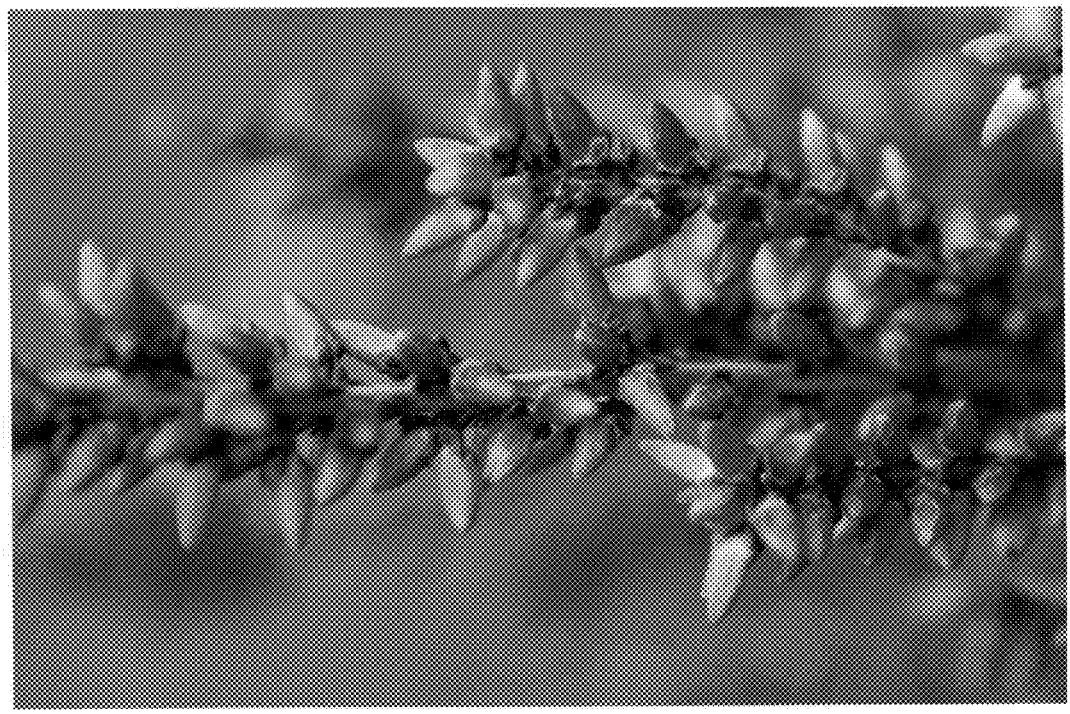

The photograph in FIG. 2 provides a close-up view of the flowers of 'Nr 5157'.

Figure 1:
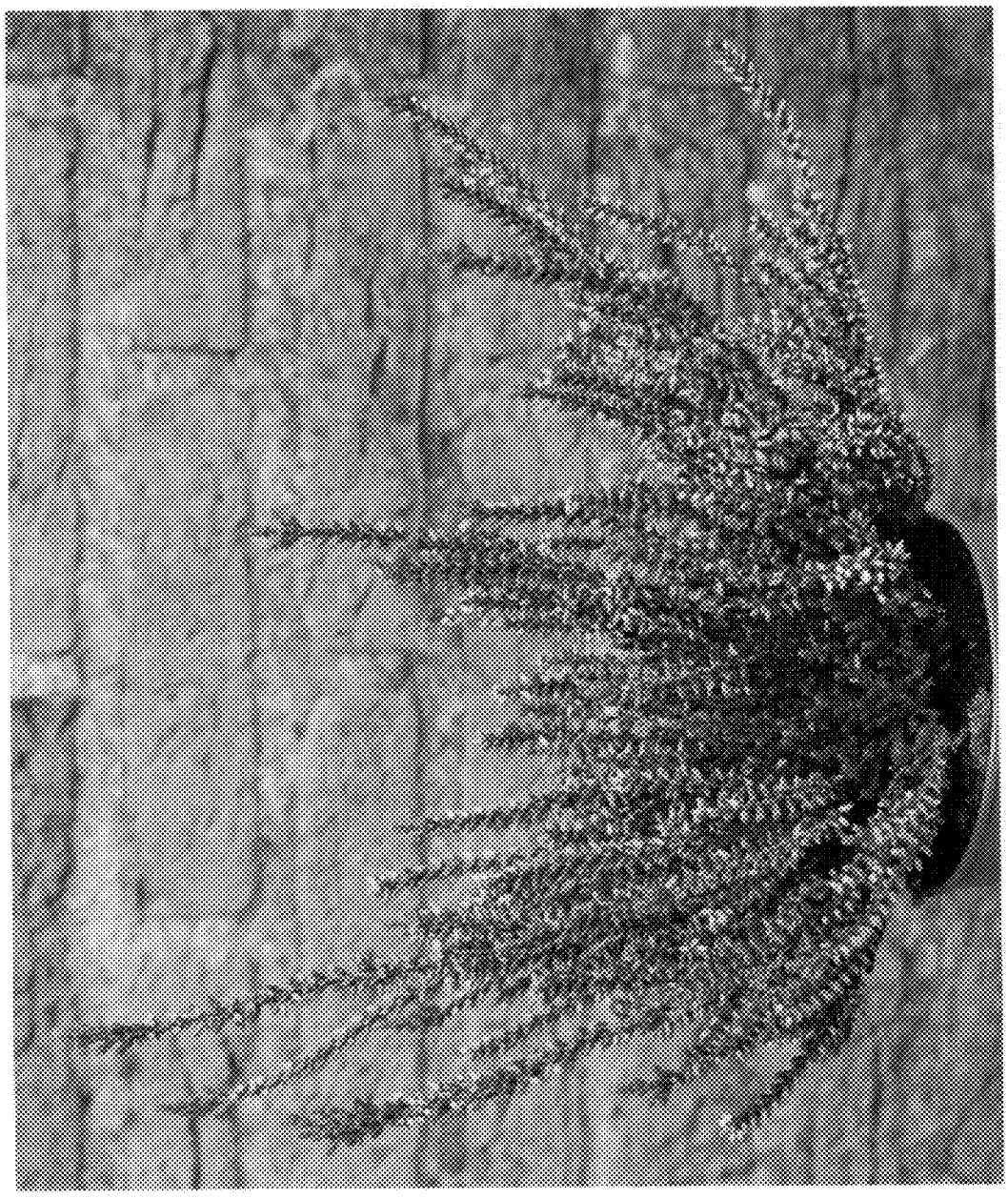
Figure 3:
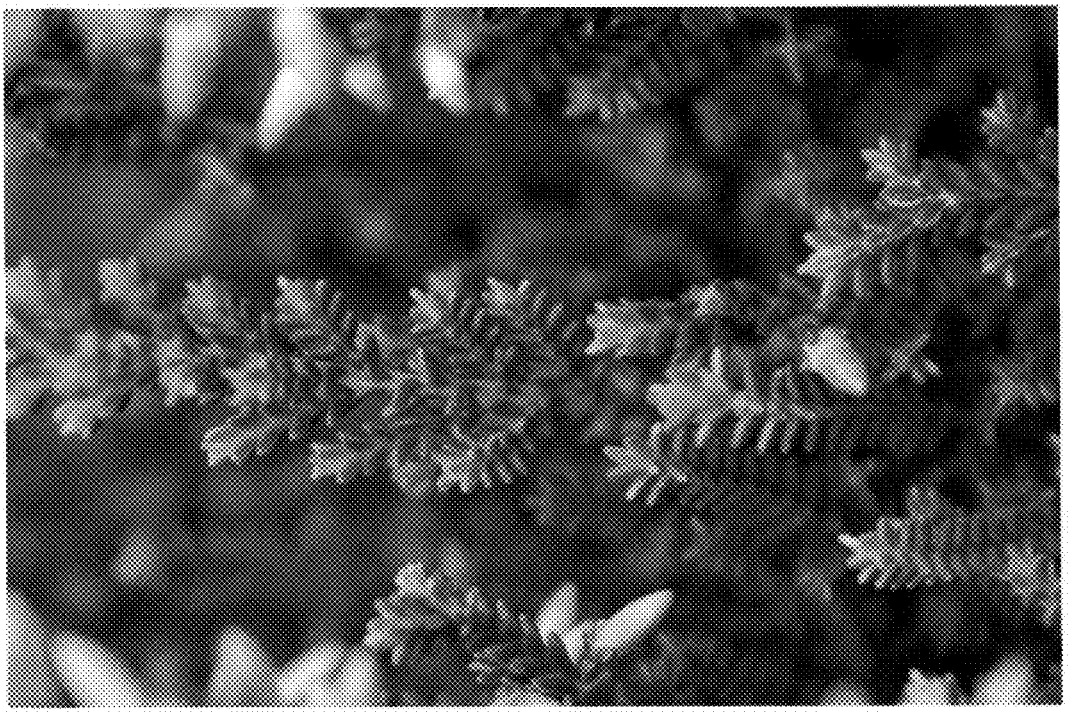

The photograph in FIG. 3 provides a close-up view of the foliage of 'Nr 5157'.

The Colors in the photograph may differ slightly from the color values cited in the detailed botanical description, which accurately describe the colors of the new *Calluna.*

DETAILED BOTANICAL DESCRIPTION

The following is a detailed description of 2 year-old plants of the new cultivar as grown outdoors in 10 cm containers in Wezep, The Netherlands. The plants were grown with an average day temperature of 14° to 30° C. and an average night temperature of 5° to 15° C. under ambient light. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms from late summer into early fall in Wezep, The Netherlands.

*Plant habit.*—Densely foliaged and flowering, upright, evergreen shrub.

*Height and spread.*—Reaches about 26.2 cm in height and 30 cm width (2 year-old plant).

*Hardiness.*—Cold hardy to U.S.D.A. Zone 4 and withstands temperatures of at least 35° C.

*Diseases resistance.*—No particular resistance or susceptibility has been observed.

*Root description.*—Fine.

Growth and propagation:

*Propagation.*—Stem cuttings.

*Root initiation.*—Roots develop in about 20 days in summer with temperatures beteen 20° and 25° C. (30 days in spring) under greenhouse conditions with ten the first 10 days under plastic.

*Growth rate.*—Vigorous.

Stem description:

*Stem shape.*—Round.

*Stem strength.*—Strong.

*Stem color.*—152A.

*Stem size.*—Lateral branches are an average of 10.4 cm in length and 1 mm in diameter.

*Stem surface.*—Slightly glossy and densely covered with very short, fine hairs.

*Stem aspect.*—Nearly upright to main stems.

*Internode length.*—Average of 1 mm.

*Branching.*—Freely branched from base with 10 main stems with an average of 17 lateral branches per main branch.

Foliage description:

*Leaf shape.*—Oblong.

*Leaf division.*—Simple.

*Leaf base.*—Decurrent.

*Leaf apex.*—Obtuse.

*Leaf fragrance.*—None.

*Leaf venation.*—None visible.

*Leaf margins.*—Entire and sparsely covered with very short, fine hairs.

*Leaf arrangement.*—Opposite.

*Leaf attachment.*—Sessile.

*Leaf number.*—About 208 per lateral branch.

*Leaf surface.*—Glabrous and slightly glossy on upper and lower surface.

*Leaf size.*—Average of 2 mm in length and 0.5 mm in width.

*Leaf color.*—Newly expanded leaves upper and lower surface; 143A, mature leaves upper and lower surface; 137A.

Inflorescence description: (flower descriptions refer to mature flower buds)

*Flower type.*—Solitary or in small clusters of flower buds borne at the leaf axils, flowers remain in the bud stage and do not open.

*Flower fragrance.*—None.

*Flower lastingness.*—Average of 4 weeks, self cleaning.

*Flower bud description.*—Immature; ovate in shape, an average of 1.8 mm in length and 1.5 mm in width, glabrous surface, N74C in color with base of bud 157D in color.

*Flower quantity.*—Average of 54 per lateral stem, over 9,000 per plant (2 years in age).

*Flower aspect.*—Held outward to upright.

*Flower shape.*—Ovate.

*Flower size.*—An average of 4 mm in depth and 2 mm in diameter.

*Peduncles.*—Average of 1 mm in length and 0.4 mm in diameter with an average angle to stem of 45°, 144A in color, moderate in strength, surface glabrous.

*Pedicels.*—None.

*Calyx form.*—Rotate in form, average of 1 mm in length and 2 mm in diameter.

*Sepals.*—5, average of 1 mm in length, 0.5 mm in width, broadly ovate in shape, entire margin, rounded apex, cuneate base, surface is smooth and dull in appearance, color of inner and outer surface 143A when bud is immature, 137A when bud is mature.

*Petals.*—5, only outer surface is visible as they remain closed, about 4 mm in length and 1.2 mm in width, ovate in shape, entire margin, bluntly acute apex, surface is velvety and glossy in appearance, color when first showing color (both surfaces); N74C with base 157D, color when mature (both surfaces); 77A to 77B to N77B, non-fading

*Petaloids.*—Enclosed by unopened bud, 5, about 2.5 mm in length and 1 mm in width, ovate in shape, entire margin, bluntly acute apex, surface and color is the same as the petals.

Reproductive organs:

*Stamens.*—None present, flowers are pistillate.

*Pistils.*—1, about 3 mm in length, stigma is club-shaped and 180D in color, style is an average of 2.8 mm in length and 180D with base 144B in color, ovary is 143A in color.

*Fruit and seed.*—None have been observed to form.

It is claimed:

1. A new and distinct cultivar of *Calluna* plant named 'Nr 5157' as herein illustrated and described.

* * * * *